United States Patent
van Putten et al.

(10) Patent No.: US 11,332,454 B2
(45) Date of Patent: *May 17, 2022

(54) PROCESS FOR THE CONVERSION OF A SOLID LIGNOCELLULOSIC MATERIAL

(71) Applicant: Furanix Technologies B.V., Amsterdam (NL)

(72) Inventors: Robert-Jan van Putten, Amsterdam (NL); Benjamin McKay, Amsterdam (NL); Gerardus Johannes Maria Gruter, Amsterdam (NL); Jan Cornelis van der Waal, Amsterdam (NL)

(73) Assignee: Furanix Technologies B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/965,746

(22) PCT Filed: Jan. 31, 2019

(86) PCT No.: PCT/EP2019/052437
§ 371 (c)(1),
(2) Date: Jul. 29, 2020

(87) PCT Pub. No.: WO2019/149853
PCT Pub. Date: Aug. 8, 2019

(65) Prior Publication Data
US 2021/0032216 A1 Feb. 4, 2021

(30) Foreign Application Priority Data
Jan. 31, 2018 (NL) .................................... 2020355

(51) Int. Cl.
*C07D 307/50* (2006.01)
*B01D 11/02* (2006.01)

(52) U.S. Cl.
CPC ........ *C07D 307/50* (2013.01); *B01D 11/0284* (2013.01); *B01D 2251/502* (2013.01)

(58) Field of Classification Search
CPC .................................................. C07D 307/50
See application file for complete search history.

(56) References Cited

U.S. PATENT DOCUMENTS

| 2,778,751 A | 1/1957 | Riehm | |
|---|---|---|---|
| 10,093,637 B2 * | 10/2018 | van Putten | C07D 307/46 |

FOREIGN PATENT DOCUMENTS

| EE | 20130003 A | 10/2014 |
|---|---|---|
| EP | 1878480 A1 | 1/2008 |
| FR | 3008409 A1 | 1/2015 |
| WO | 2007/111605 A1 | 10/2007 |
| WO | 2009/114843 A1 | 9/2009 |
| WO | 2012/061085 A2 | 5/2012 |
| WO | 2014/062303 A2 | 4/2014 |
| WO | 2014/066746 A1 | 5/2014 |
| WO | 2015/136044 A1 | 9/2015 |
| WO | 2018/041975 A1 | 3/2018 |

OTHER PUBLICATIONS

Vicente et al., "Oxidation of 5-chloromethylfurfural (CMF) to 2,5-diformylfuran (DFF)", Molecules (2017) vol. 22, pp. 1-14.
Mascal et al., "Dramatic Advancements in the Saccharide to 5-(Chloromethyl)furfural Conversion Reaction", published in ChemSusChem (2009), vol. 2, pp. 859-861.
Mascal, Mark, "Comment on Gao, W., et al. 'Efficient One-Pot Synthesis of 5-Chloromethylfurfural (CMF) from Carbohydrates in Mild Biphasic Systems', Molecules 2013, 18, 7675-7685", Molecules 2014, 19, 1367-1369.
Gao, et al., "Correction: Gao, W., et al. Efficient One-Pot Synthesis of 5-Chloromethyl-furfural (CMF) from Carbohydrates in Mild Biphasic Systems. Molecules 2013, 18, 7675-7685", Molecules 2014, 19, 1370-1374.
Gao, et al., "Efficient One-Pot Synthesis of 5-Chloromethylfurfural (CMF) from Carbohydrates in Mild Biphasic Systems", Molecules 2013, 18, 7675-7685.

* cited by examiner

*Primary Examiner* — Golam M Shameem
(74) *Attorney, Agent, or Firm* — Hoffmann & Baron, LLP (57) ABSTRACT

A process for the conversion of solid lignocellulosic material containing hemicellulose, cellulose and lignin, includes (a) hydrolyzing, at a temperature equal to or less than 40° C. at least part of the hemicellulose and at least part of the cellulose of the solid lignocellulosic material with an aqueous hydrochloric acid solution, containing in the range from equal to or more than 40.0 wt. % to equal to or less than 51.0 wt. % hydrochloric acid, based on the combined weight amount of water and hydrochloric acid in the aqueous hydrochloric acid solution; yielding a hydrochloric acid-containing, aqueous hydrolysate solution; (b) separating the hydrochloric acid-containing, aqueous hydrolysate solution from the lignin; and (c) heating at least part of the hydrochloric acid-containing, aqueous hydrolysate solution to a temperature equal to or more than 60° C., yielding a product solution containing 5-(chloromethyl)furfural, and extracting the 5-(chloromethyl)furfural from the product solution into an extraction solvent.

22 Claims, 2 Drawing Sheets

PROCESS FOR THE CONVERSION OF A SOLID LIGNOCELLULOSIC MATERIAL

CROSS-REFERENCE TO RELATED APPLICATIONS

This application is the National Stage of International Application No. PCT/EP2019/052437, filed Jan. 31, 2019, which claims the benefit of Netherlands Application No. 2020355, filed Jan. 31, 2018, the contents of which is incorporated by reference herein.

FIELD OF THE INVENTION

The present invention relates to a process for the conversion of a solid lignocellulosic material.

BACKGROUND TO THE INVENTION

In recent times use of sustainable resources, such as biomass, is becoming increasingly important for the production of compounds for fuel and chemical applications. Such bio-derived fuels and chemicals are also sometimes referred to as "biofuels" and "biochemicals". One of the advantages of using sustainable biomass resources is that the $CO_2$ balance is more favorable as compared with a conventional feedstock of a mineral source. The production of biofuels and biochemicals from a non-edible sustainable resource, such as solid lignocellulosic material, is preferred, as such non-edible solid lignocellulosic material does not compete with food production.

5-(Chloromethyl)furfural is a valuable intermediate in the production of biofuels and biochemicals. It can be used as an intermediate in the production of, for example, 5-(hydroxymethyl)furfural (HMF), 5-(alkoxymethyl)furfural and/or 2,5 di-formylfuran (DFF), also referred to as 2,5-furandicarbaldehyde.

2,5-Di-formylfuran may serve as a monomer or cross-linking agent in the preparation of polymers, but can also be used as a binding agent, as a corrosion-inhibiting agent or as a surface treatment agent for certain metals. It can also be used as a precursor for 2,5-furan-dicarboxylic acid (FDCA), a monomer building block for the production of bio-based polyethylenefuranoate (PEF). 2,5-Di-formylfuran can be produced from 5-(chloromethyl)furfural as described, for example, in French patent application no. FR3008409. Further, the oxidation of 5-chloromethylfurfural to 2,5-diformylfuran is described in the article of Vicente et al., titled "Oxidation of 5-chloromethylfurfural to 2,5-diformylfuran", published in Molecules (2017) vol. 22, page 329 and following.

5-(Alkoxymethyl)furfural compounds are interesting both for fuel (additives) and chemical applications. For example, 5-(ethoxymethyl) furfural (EMF) is an interesting diesel fuel additive. Further, for example 5-(methoxymethyl)furfural (MMF) is an important intermediate in the production of 2,5-furan-dicarboxylic acid (FDCA). Estonian patent application EE2013/0003A describes a method for the preparation of 5-(alkoxymethyl)furfurals from 5-(chloromethyl)furfural or 5-(bromomethyl)furfural.

It is therefore desirable to have a process that would allow one to produce 5-(chloromethyl)furfural from a solid lignocellulosic material.

The article by Mascal et al. titled "Dramatic Advancements in the Saccharide to 5-(Chloromethyl)furfural Conversion Reaction", published in ChemSusChem (2009), vol 2, pages 859-861, describes a process for the conversion of corn stover into 5-(chloromethyl)furfural in a biphasic reactor, for example by heating powdered corn stover, concentrated hydrochloric acid (HCl) and 1,2-dichloroethane with vigorous stirring at 80° C.

The process as described by Mascal, however, is not attractive for the conversion of a solid lignocellulosic material on a commercial scale.

Solid lignocellulosic materials contain not only cellulose, but also contain hemicellulose and lignin. When contacted with concentrated hydrochloric acid at high temperatures, as in the Mascal process, the hemicellulose and cellulose are converted to various pentoses (C5-saccharides) and hexoses (C6-saccharides). Under the conditions of the Mascal process, such pentoses and hexoses react with lignin in various types of reactions resulting in non-profitable side-products and/or contaminants. In a commercial-scale process such non-profitable side-products would further have to be repeatedly removed, making the overall process complex, expensive and economically unattractive.

The Mascal process is further disadvantageous in that the complete solid lignocellulosic material is heated. Not only the hemicellulose and cellulose fraction are heated, but also the lignin fraction. The heated lignin, however, cannot be converted in any useful product. When converting a whole lignocellulosic material in a process as described by Mascal, valuable energy, reactants and reactor volume is wasted.

The residual lignin produced in a Mascal process is also problematic. Residual lignin from a biomass-degradation process is normally incinerated. However, any residual lignin obtained after treatment with concentrated hydrochloric acid at high temperatures in a process as described by Mascal can contain high concentrations of covalently bound chlorine. This makes such residual lignin produced in a Mascal process less interesting for incineration.

Further the Mascal process requires powdering of the solid lignocellulosic feedstock and very vigorous stirring of the reaction mixture. The reduction of the particle size of a solid lignocellulosic feedstock to a powder and vigorous stirring of a reaction mixture may be handled relatively easy at laboratory scale but can be very cumbersome and energy-consuming when handling large amounts of feedstock at a commercial scale.

WO2014/066746 describes methods to produce 5-(halomethyl)furfural, including 5-(chloromethyl)furfural, by acid-catalyzed conversion of biomass. It is described that the biomass may be pretreated to help make the sugars in the biomass more accessible, by disrupting the crystalline structures of cellulose and hemicellulose and breaking down the lignin structure (if present). Common pretreatments mentioned include mechanical treatment (e.g., shredding, pulverizing, grinding), concentrated acid and dilute acid. In the exemplified process a biomass containing cellulose and/or hemicellulose is added to a reactor and contacted with solvent and aqueous hydrochloric acid. Reaction temperatures between 30° C. and 300° C. are mentioned. However, also in this process, lignin remains present as part of the feedstock. Commercialization of this process thus suffers from the same disadvantages and complications as the Mascal process.

It would therefore be an advancement in the art to provide a process for the production of 5-(chloromethyl)furfural from a solid lignocellulosic material that does not suffer from the above disadvantages and complications related to lignin and/or which can be more easily scaled up to a commercial-scale and/or provides a more efficient conversion to 5-(chloromethyl)furfural. It would be an even further advancement if such a process could be operated in a continuous or semi-continuous manner.

SUMMARY OF THE INVENTION

Such a process has now been obtained with the process according to the invention.

Accordingly the present invention provides a process for the conversion of a solid lignocellulosic material containing hemicellulose, cellulose and lignin, the process including the following steps:

(a) hydrolyzing, at a temperature equal to or less than 40° C., preferably equal to or less than 30° C., at least part of the hemicellulose and at least part of the cellulose of the solid lignocellulosic material with an aqueous hydrochloric acid solution, containing in the range from equal to or more than 40.0 wt. % to equal to or less than 51.0 wt. % hydrochloric acid, based on the combined weight amount of water and hydrochloric acid in such aqueous hydrochloric acid solution; yielding a hydrochloric acid-containing, aqueous hydrolysate solution;

(b) separating the hydrochloric acid-containing, aqueous hydrolysate solution from the lignin; and (c) heating at least part of the hydrochloric acid-containing, aqueous hydrolysate solution to a temperature equal to or more than 60° C., yielding a product solution containing 5-(chloromethyl)furfural, and extracting the 5-(chloromethyl)furfural from such product solution into an extraction solvent.

Such process is suitably yielding a 5-(chloromethyl)furfural-containing extraction solvent.

In the process according to the invention, lignin can be elegantly removed before the production of 5-(chloromethyl)furfural. In addition, also undesired impurities entrained in the lignin can be removed in this way. Thus, the disadvantages and complications of the Mascal process and the process described in WO2014/066746 can be avoided.

The process according to the invention can be easily scaled up to an economically attractive commercial-scale process. The process can further be suitably operated in a continuous or semi-continuous manner as described in more detail below.

Further step (a) of the process according to the invention can be carried out at a lower temperature than the Mascal process or the process described in WO2014/066746. As a result any residual lignin retrieved from the process according to the invention can be expected to be lower in covalently bound chlorine.

In addition, the process according to the invention allows for a very economical separation of the hydrochloric acid. Hydrochloric acid is a compound that is cumbersome and expensive to separate from saccharides, such as the saccharides in an aqueous hydrolysate solution. By forwarding the hydrochloric acid-containing aqueous hydrolysate solution directly into step (c), without separating the hydrochloric acid, expensive and cumbersome process steps for the removal of hydrochloric acid, when isolating the saccharides, are no longer needed and can be avoided. After conversion of at least part of the saccharides in the aqueous hydrolysate solution to 5-(chloromethyl)furfural, such 5-(chloromethyl)furfural can be extracted in an easy and economically attractive manner by means of the mentioned extraction in step (c). As explained in more detail below, the concurrent extraction of the 5-(chloromethyl)furfural from the product solution into an extraction solvent in step (c) advantageously further increases the economic attractiveness of the process.

The 5-(chloromethyl)furfural may or may not be separated from the extraction solvent. Subsequently the 5-(chloromethyl)furfural, whether or not in the presence of the extraction solvent, may suitably be used in a subsequent process for the production of 2,5 di-formylfuran (DFF), 5-(hydroxymethyl)furfural (HMF) and/or 5-(alkoxymethyl) furfurals, such as 5-(methoxymethyl)furfural (MMF) or 5-(ethoxymethyl)furfural (EMF).

DETAILED DESCRIPTION OF THE INVENTION

By a lignocellulosic material is herein understood a material that contains cellulose, hemicellulose and lignin. By cellulose (also herein referred to as cellulosic material) is herein understood a homopolysaccharide comprising glucose-based monomer units, such as cellobiose. Hemicellulose (also herein referred to as hemicellulosic material) is also a polysaccharide, but differs from cellulose. Hemicelluloses may for example comprise pentose monomer units, such as xylose and arabinose, hexose monomer units, such as glucose and mannose, hexuronic acid and deoxy-hexose based monomer units. Whereas some hemicelluloses may essentially consist of only one single type of monomer unit (for example xylans comprising essentially only xylose), other hemicelluloses may comprise several different types of monomer units (such as for example glucomannans comprising glucose and mannose).

The process according to the invention can use a wide variety of solid lignocellulosic materials as feedstock. Examples of solid lignocellulosic materials that may suitably be used in the process of the invention include for example agricultural wastes such as stover (for example corn stover and soybean stover), corn cobs, rice straw, rice hulls, oat hulls, corn fibre, cereal straws such as wheat, barley, rye and oat straw; grasses; forestry products and/or forestry residues such as wood and wood-related materials such as sawdust and bark; paper waste; sugar processing residues such as bagasse and beet pulp; or mixtures thereof. More preferably the solid lignocellulosic material is selected from the group consisting of wood, sawdust, bark, straw, hay, grasses, bagasse, corn stover and/or mixtures thereof.

Preferably the solid lignocellulosic material is non-edible, to prevent the process from being in competition with food-production. Most preferably the solid lignocellulosic material comprises or consists of wood. The wood may include soft wood and/or hard wood and may originate from all types of trees, including spruce, pine, willow, larch, oak, birch, poplar, eucalyptus and other trees.

Different types of wood may contain different amounts of cellulose and hemicellulose. In addition, as illustrated in Table 5-1 of Fengel & Wegener in their handbook titled "Wood: Chemistry, ultrastructure, reactions," (1984) published by Walter De Gruyter, Berlin-New York, different types of wood may contain different types and amounts of non-glucosic units in the hemicellulose fraction. Non-glucosic units are monomer units other than glucose-based monomer units.

Depending on market demand for certain side-products, some types of wood may be more preferred than others. For example, in the process according to the invention furfural can conveniently be co-produced from xylose. If there is a substantial market demand for furfural, the solid lignocellulosic material is preferably wood or a wood-related material, having equal to or more than 10 wt. % (weight percent) xylose units, based on the total weight of its non-glucosic units. Examples of suitable wood types for this purpose include Acer rubrum, Betula alleghaniensis, Betula papyrifera, Betula verrucosa, Fagus grandiptia, Fraxinus excelsior, Populus tremuloides, Robinia pseudoacacia and Ulmus Americana. The hydrochloric acid-containing, aqueous hydrolysate solution yielded in step (a) will then suitably contain saccharides containing xylose. In this way the process according to the invention conveniently allows one to co-produce furfural.

If it is desired to maximize the production of 5-(chloromethyl)furfural, a lignocellulosic material containing high amounts of epimers of glucose, such as mannose or galactose, can be used. Examples of suitable wood types for this purpose include Abies balsamea, Larix decidua, Larix laricina, Picea abies, Picea glauca, Pinus sylvestris and Tsugo Canadensis. In such a case the lignocellulosic material is preferably wood or a wood-related material, comprising equal to or more than 10 wt. % mannose units, based on the total weight of non-glucosic units in the hemicellulose fraction.

If it is desired to produce 5-(chloromethyl)furfural and minimize side-product make, a lignocellulosic material containing a low amount of hemicellulose can be used.

The solid lignocellulosic material may conveniently be washed, dried, roasted, torrefied and/or reduced in particle size before it is used in step (a). The solid lignocellulosic material may conveniently be supplied or be present in a variety of forms, including chips, pellets, powder, chunks, briquettes, crushed particles, milled particles, ground particles or a combination of two or more of these. When the solid lignocellulosic material is wood, it can for example be supplied or be present in the form of wood powder, wood chips, wood pellets, wood briquettes, wood chunks or a combination of two or more of these.

Preferably the solid lignocellulosic material in the present process is a solid lignocellulosic material of which the particles preferably have a particle size of at least P16A and at most P100, preferably P45A or P45B, conforming European standard EN 14961-1 on solid biofuels. Alternatively, the solid lignocellulosic material in the present process is a solid lignocellulosic material of which the particles preferably have a minimum size of 3 mm and maximum size of 100 mm, and more preferably have a size of between 8 mm and 45 mm, as measured following European standard EN 15149 on solid biofuels.

When the solid lignocellulosic material is wood, such wood is most preferably supplied or present in the form of wood chips. When the solid lignocellulosic material comprises grass, bagasse and/or stover, such grass, bagasse and/or stover is most preferably supplied or present in the form of pellets. Such pellets advantageously provide unstructured biomass, such as grass, bagasse and/or stover, with a desired morphology. Such morphology can advantageously limit the collapse of the material inside the reactors upon hemicellulose and cellulose hydrolysis, which otherwise could result in an undesired pressure drop.

Preceding to step (a), the solid lignocellulosic material can be provided to a reactor, suitably in any manner known by the person skilled in the art. The lignocellulosic material can for example be provided to a reactor by means of a feed hopper, conveyer belt, screw feeder or a combination thereof. The solid lignocellulosic material may suitably be loaded into such a reactor in a batch-wise, semi-continuous or continuous manner. Preferably the solid lignocellulosic material is loaded into a reactor via one or more inlets located at the top of such a reactor and/or via one or more lateral inlets located in the reactor wall, preferably in a continuous or semi-continuous manner.

The solid lignocellulosic material is preferably packed in a, suitably essentially vertical, tubular reactor. The reactor can suitably be provided with a discharge opening that can be opened and closed, to allow for discharge of any residual lignin after the process. Preferably such a discharge opening is located at the bottom of such a reactor.

Step (a) suitably comprises hydrolyzing at least part of the solid lignocellulosic material (i.e. at least part of the hemicellulose and at least part of the cellulose of the solid lignocellulosic material), at a temperature equal to or less than 40° C., preferably equal to or less than 30° C. The solid lignocellulosic material is hydrolyzed with an aqueous hydrochloric acid solution, containing in the range from equal to or more than 40.0 wt. % to equal to or less than 51.0 wt. % hydrochloric acid, based on the combined weight amount of water and hydrochloric acid in such aqueous hydrochloric acid solution. Such step (a) is suitably yielding a hydrochloric acid-containing, aqueous hydrolysate solution. The term "hydrolysate" is well known by persons skilled in the art to refer to product(s) of hydrolysis.

Step (a) is preferably carried out in a plurality of reactors, preferably connected in series. Such plurality of reactors is herein also referred to as a reactor sequence. Any reactor(s) used in step (a) are herein also referred to as hydrolysis reactor(s).

Preferably, step (a) is carried out in a plurality of reactors (also referred to as columns) connected in series as described for a Bergius-Rheinau process. Examples of the Bergius-Rheinau process include the Bergius-Rheinau process, preferably as amended by Riehm, as described in for example U.S. Pat. No. 2,778,751. It is also possible for step (a) to be carried out in a plurality of reactors as described in WO2012/061085.

Preferably, step (a) is carried out semi-continuously, preferably during one or more sequential cycle periods. By a cycle period can herein suitably be understood a time period within which one cycle is performed, as illustrated in the examples. Each cycle period preferably has a duration in the range of equal to or more than 4 hours to equal to or less than 24 hours, more preferably in the range from equal to or more than 6 hours to equal to or less than 12 hours, and most preferably a duration in the range from equal to or more than 7 hours to equal to or less than 9 hours. For example, the cycle period can be 8 hours.

Preferably step (a) is carried out in a plurality of reactors, preferably connected in series, wherein one or more portions of the aqueous hydrochloric acid solution are moving from one reactor to another and are contacted with, optionally partially hydrolyzed, stationary (parts of) the solid lignocellulosic material. These optionally partially hydrolyzed, stationary (parts of) the solid lignocellulosic material, can suitably be packed or otherwise residing in the reactors. As after partial hydrolysis the original solid lignocellulosic material may no longer be complete, such partially hydrolyzed lignocellulosic material, including partially hydrolyzed hemicellulose and/or partially hydrolyzed cellulose, is herein also referred to as simply partially hydrolyzed "material".

More preferably, the aqueous hydrochloric acid solution is contacted counter-currently with the, optionally partially hydrolyzed, solid lignocellulosic material, respectively the hemicellulosic and cellulosic material.

Preferably, in step (a) one or more portions of aqueous hydrochloric acid solution can conveniently form a plug or liquid column, optionally in combination with other fluids, which plug or liquid column is moving continuously or semi-continuously, preferably in a counter-current direction, through a plurality of reactors, each reactor containing an amount of stationary, optionally already partially hydrolyzed, material.

When step (a) is carried out counter-currently, one or more portions of fresh aqueous hydrochloric acid solution may conveniently be supplied to a reactor holding material which has already been partially hydrolyzed. Saccharides can be absorbed from such, already partially hydrolyzed, material and the one or more portions of aqueous hydrochloric acid solution (suitably now containing some saccharides) may subsequently move from the outlet of such reactor to the inlet of a preceding reactor, which preceding reactor holds material which has undergone less or no hydrolysis.

After absorbing saccharides, the aqueous hydrochloric acid solution is no longer fresh and is herein also referred to as aqueous intermediate hydrolysate solution. Hence, by a, hydrochloric acid-containing, aqueous intermediate hydrolysate solution is herein understood an aqueous hydrochloric acid solution further containing saccharides. Such aqueous intermediate hydrolysate solution suitably thus comprises saccharides and hydrochloric acid, suitably in a hydrochloric acid concentration in the range from equal to or more than 40.0 wt. % to equal to or less than 51.0 wt. %, based on the combined weight amount of water and hydrochloric acid in such solution. More preferred concentrations are described below for the aqueous hydrochloric acid solution. It is also possible for the aqueous intermediate hydrolysate solution to slowly become more diluted, when moving from one reactor to a next reactor. The aqueous intermediate hydrolysate solution may, however, suitably still be used for contacting further, optionally partially hydrolyzed, material to suitably absorb further saccharides therefrom. Whilst moving, preferably counter-currently, from one reactor to another reactor, the aqueous intermediate hydrolysate solution can gradually become more and more saturated with saccharides until finally a sufficiently saturated, hydrochloric acid-containing, aqueous hydrolysate solution is yielded, that can be separated in step (b).

When carried out counter-currently, step (a) is preferably carried out in a plurality of "y" reactors $R_1$ to $R_y$, connected in series, wherein fresh solid lignocellulosic material, containing hemicellulose and cellulose, is residing or is introduced in reactor $R_1$, and each subsequent reactor $R_2$ to $R_y$ contains partially hydrolyzed material, where the degree of hydrolysis of the material increases in the direction of $R_2$ to $R_y$; and wherein one or more portions of fresh aqueous hydrochloric acid solution are introduced in the last reactor $R_y$ and move counter-currently from reactor $R_y$ to reactor $R_1$, and wherein such portions of aqueous hydrochloric acid solution gradually absorb saccharides from the, optionally already partially hydrolyzed, material, to thereby produce a hydrochloric acid-containing, aqueous hydrolysate solution, that can be withdrawn from reactor $R_1$. Such hydrochloric acid-containing, aqueous hydrolysate solution will be advantageously more rich in saccharides, than if step (a) would have been carried out in a single reactor. Suitably, in reactor $R_y$, a residue comprising lignin (also referred to as "residual lignin") stays behind, that can suitably be discarded from the reactor $R_y$. Preferably "y" is a number in the range from equal to or more than 2 to equal to or less than 16, more preferably in the range from equal to or more than 4 to equal to or less than 8.

Hence, preferably step (a) comprises hydrolyzing the hemicellulose and the cellulose of the solid lignocellulosic material at a temperature equal to or less than 30° C. with an aqueous hydrochloric acid solution, containing in the range from equal to or more than 40.0 wt. % to equal to or less than 51.0 wt. % hydrochloric acid, based on the combined weight amount of water and hydrochloric acid in such aqueous hydrochloric acid solution, wherein the lignocellulosic material is contacted counter-currently, in a plurality of reactors connected in series, with the aqueous hydrochloric acid solution, yielding a, hydrochloric acid-containing, aqueous hydrolysate solution.

Preferably step (a) is carried out in a plurality of reactors, preferably connected in series, comprising 2 or more reactors, more preferably in the range from equal to or more than 2 to equal to or less than 16 reactors, still more preferably in the range from equal to or more than 4 to equal to or less than 8 reactors and most preferably in the range from equal to or more than 4 to equal to or less than 7 reactors.

Step (a) can advantageously be carried out in a continuous or semi-continuous manner. For example, step (a) can be carried out within a continuously repeating cycle. Preferably, in such continuously repeating cycle:

step (a) is carried out in a reactor sequence of "y" reactors $R_1$ to $R_y$, wherein fresh lignocellulosic material is residing in reactor $R_1$ and each subsequent reactor $R_2$ to $R_y$ contains partially hydrolyzed lignocellulosic material, and wherein one or more portions of fresh aqueous hydrochloric acid solution are introduced in the last reactor $R_y$, pushing forward a liquid column, such liquid column containing previous portions of aqueous hydrochloric acid solution, in a counter-current direction from reactor $R_y$ to reactor $R_1$, to thereby yield a residue residing in reactor $R_y$ and a hydrochloric acid-containing, aqueous hydrolysate solution, which hydrochloric acid-containing, aqueous hydrolysate solution is recovered from reactor $R_1$; and the residue is unloaded from reactor $R_y$;

whereafter:

respective reactors $R_1$ to $R_{y-1}$ shift into the position previously occupied by respective reactors $R_2$ to $R_y$, and respective reactor $R_y$ shifts into the position previously occupied by respective reactor $R_1$.

The cycle period is suitably the time period wherein all the above listed activities are to be carried out, whereafter each reactor can shift one position in the reactor sequence. For example, when the process is carried out in a reactor sequence of "y" reactors $R_1$ to $R_y$, the cycle period can thus suitably be the period between the preceding shift in the reactor sequence and the subsequent shift in the reactor sequence. Starting at t=0, with "y" reactors, after "y" cycle periods the reactor sequence suitably has again the same configuration as at t=0.

The residue may suitably comprise residual lignin.

The aqueous solutions used in the cycle and any optional intermediate inert fluid can enter a reactor via an inlet located in the top of the reactor, bottom of the reactor or in the reactor wall near the top, respectively bottom, of the reactor. The aqueous solutions and any optional intermediate inert fluid can suitably leave the reactor at the opposite side of such inlet.

The cycle time can vary widely, but preferably ranges from equal to or more than 4 hours, more preferably from equal to or more than 6 hours, to equal to or less than 12 hours, more preferably to equal to or less than 9 hours.

The reactor(s) in which step (a) can be carried out, are herein also referred to as "hydrolysis reactor(s)". Such hydrolysis reactors are preferably tubular reactors comprising a packed bed of solid lignocellulosic material, such as e.g. wood chips. The hydrolysis reactor(s) can for example comprise a cylindrical vessel with its axis arranged in an essentially vertical or essentially horizontal manner. Preferably the hydrolysis reactor(s) comprise(s) a cylindrical vessel with its axis arranged in an essentially vertical manner. The reactor(s) may be slightly tilted towards an angle to allow for an easier discharge of residue. Examples of suitable reactors include the reactors as described in for example U.S. Pat. No. 2,778,751, EP1878480, WO2015/136044 and non-prepublished PCT/EP2017/071914. The aqueous hydrochloric acid containing solution can advantageously flow through such hydrolysis reactors in a continuous or semi-continuous manner.

Step (a) is advantageously carried out at a relatively low temperature, i.e. at a temperature equal to or less than 30° C. For practical purposes step (a) can suitably be carried out at a temperature in the range from equal to or more than 0° C., more preferably equal to or more than 5° C., and still more preferably equal to or more than 10° C., to equal to or less than 29° C., more preferably equal to or less than 25° C.

Step (a) can be carried out at a wide range of pressures. Preferably, however, step (a) is carried out at an ambient pressure of about 0.1 MegaPascal (MPa). All pressures mentioned herein are absolute pressures.

Preferably the aqueous hydrochloric acid solution has a hydrochloric acid concentration in the range from equal to or more than 41.0 wt. % to equal to or less than 45.0 wt. %, based on the combined weight amount of water and hydrochloric acid in such aqueous hydrochloric acid solution.

Step (a) is suitably yielding a hydrochloric acid-containing, aqueous hydrolysate solution. By a hydrolysate solution is herein understood a solution comprising hydrolysis products.

The aqueous hydrolysate solution may suitably contain saccharides and hydrochloric acid.

The aqueous hydrolysate solution may suitably comprise mono- di- and/or oligo-saccharides. By an oligo-saccharide is herein understood a saccharide comprising 3 to 10 monosaccharide units.

During the hydrolysis in step (a) part or whole of the hemicellulose present in the lignocellulosic material and part or the whole of the cellulose present in the lignocellulosic material can be hydrolyzed. Such hydrolysis can suitably result in a mixture of mono- di- and oligo-saccharides of pentoses (i.e. $C_5$-saccharides, that is, sugars whose molecules contain five carbon atoms) and hexoses (i.e. $C_6$-saccharides, that is, sugars whose molecules contain six carbon atoms).

The aqueous hydrolysate solution may include for example pentose monosaccharides, hexose monosaccharides, pento se disaccharides, hexose disaccharides, and pentose-hexose disaccharides, pentose oligosaccharides, hexose oligosaccharides and/or oligosaccharides of mixtures of pentoses and hexoses. Suitably the aqueous hydrolysate solution can comprise one or more compounds selected from the group consisting of glucose, fructose, mannose, galactose, arabinose, xylose, sucrose, cellobiose, ribulose, ribose, lyxose, allose, altrose, glucose dimers (such as maltose), glucose trimers, cellotriose, maltotriose, cellodextrins, dextrins, xylan-oligosaccharides, mannan-oligosaccharides, arabinan-oligosaccharides and oligofructans. More suitably the aqueous hydrolysate solution can comprise at least one compound selected from the group consisting of mannose, glucose, galactose, arabinose and xylose.

Preferably the aqueous hydrolysate solution contains a total amount of saccharides (including mono-, di- and/or oligosaccharides) of equal to or more than 2 wt. % saccharides, more preferably of equal to or more than 5 wt. % saccharides, still more preferably of equal to or more than 10 wt. % saccharides, and most preferably of equal to or more than 20 wt. % saccharides, based on the total weight of the aqueous hydrolysate solution. The upper limit for the saccharide content in the aqueous hydrolysate solution is formed by the solubility of the saccharides in the solution. For glucose, a solubility at 25° C. of 909 grams glucose per kilogram water has been reported. For practical purposes the aqueous hydrolysate solution may suitably contain a total amount of saccharides (including mono-, di- and/or oligosaccharides) of equal to or less than 45 wt. %, more preferably of equal to or less than 40 wt. % saccharides, based on the total weight of the aqueous hydrolysate solution.

In addition to the saccharides, the aqueous hydrolysate solution will suitably contain hydrochloric acid. Preferably the aqueous hydrolysate solution will have a hydrochloric acid concentration in the range from equal to or more than 30.0 wt. % to equal to or less than 45.0 wt. %, more preferably in the range from equal to or more than 38.0 wt. % to equal to or less than 43.0 wt. %, based on the weight of the combination of hydrochloric acid and water.

Step (b) comprises separating the hydrochloric acid-containing, aqueous hydrolysate solution from the lignin. That is, the aqueous hydrolysate solution obtained by hydrolysis of at least part of the cellulose and at least part of the hemicellulose of the solid lignocellulosic material may suitably be separated from the residual lignin, that was not hydrolyzed.

The aqueous hydrolysate solution can suitably be separated from the residual lignin in any manner known to be suitable by the person skilled in the art, such as for example described in U.S. Pat. No. 2,778,751, EP1878480, WO2015/136044 and non-prepublished PCT/EP2017/071914. For example, the aqueous hydrolysate solution can be withdrawn from any hydrolysis reactor in which hydrolyzing was carried out, via one or more outlets in such a hydrolysis reactor. The residual lignin can be retained inside such a hydrolysis reactor and can be discarded at a later moment in time. The removal of residual lignin can be carried out for example in a batch or semi-continuous manner.

Suitably step (a) and step (b) can be combined, especially when operating the process or parts of the process in a semi-continuous or continuous manner.

It is advantageous to supply the part or whole of the, aqueous hydrolysate solution comprising both the hydrochloric acid and the saccharides directly into step (c).

Step (c) comprises heating at least part of the hydrochloric acid-containing, aqueous hydrolysate solution to a temperature equal to or more than 60° C., yielding a product solution containing 5-(chloromethyl)furfural, and extracting the 5-(chloromethyl)furfural from such product solution into an extraction solvent. Step (c) is thus suitably yielding a 5-(chloromethyl)furfural-containing extraction solvent.

Without wishing to be bound by any kind of theory the heating in step (c) is believed to suitably result in the dehydration of at least part of the saccharides, present in the hydrochloric acid-containing, aqueous hydrolysate solution, into 5-(chloromethyl)furfural.

Step (c) may or may not be carried out in the presence of a chloride containing promotor such as lithium chloride. Such lithium chloride may advantageously enhance the conversion of saccharides within the aqueous hydrolysate solution.

In addition, additional hydrochloric acid may or may not be added; or additional water may or may not be added or removed. The later may help to obtain an optimum hydrochloric acid concentration for step (c).

Preferably step (c) comprises heating at least part of the hydrochloric acid-containing, aqueous hydrolysate solution to a temperature equal to or more than 60° C., more preferably equal to or more than 70° C., yielding a product solution containing 5-(chloromethyl)furfural, whilst at the same time extracting the 5-(chloromethyl)furfural from such product solution into an extraction solvent. Part or whole of the produced 5-(chloromethyl)furfural can suitably be simultaneously extracted from the product solution into an extraction solvent. Preferably at least part of the 5-(chloromethyl)furfural is removed continuously or semi-continuously via in-situ liquid-liquid extraction into such extraction solvent.

Preferably, step (c) is carried out in the presence of such an extraction solvent. More preferably, step (c) comprises heating at least part of the, hydrochloric acid-containing, aqueous hydrolysate solution to a temperature equal to or more than 60° C., more preferably equal to or more than 70° C., in the presence of an extraction solvent, to thereby produce 5-(chloromethyl)furfural, and, preferably in-situ, extracting at least part of the produced 5-(chloromethyl)furfural into such extraction solvent, to thereby produce a 5-(chloromethyl)furfural-containing extraction solvent.

After conversion of the aqueous hydrolysate solution, or more precisely the saccharides in the aqueous hydrolysate solution, and the extraction of the 5-(chloromethyl)furfural from the, hydrochloric acid-containing, aqueous hydrolysate solution, such solution can suitably become depleted from 5-(chloromethyl)furfural. Suitably merely a residual, hydrochloric acid-containing, aqueous solution remains. Such residual, hydrochloric acid-containing, aqueous solution may advantageously be recycled to step (a), optionally after removal of any impurities and/or optionally after reconcentration of the hydrochloric acid. That is, preferably a hydrochloric acid-containing, residual aqueous solution is obtained, and such, hydrochloric acid-containing, residual aqueous solution is recycled to step (a), optionally after adjusting the hydrochloric acid concentration.

Step (c) of the process according to the invention can suitably be carried out batch-wise, semi-continuously or continuously, in one or more reactor(s) and/or vessel(s). These one or more reactor(s) and/or vessel(s) are herein also referred to as dehydration reactor(s) and/or vessel(s). Preferably only one reactor is used in step (c). Step (c) can be carried out in an agitated dehydration reactor or in a non-agitated reactor with counter-flow as explained in more detail below.

The reactor can for example be a bubble reactor, a plug flow reactor, an external recycle loop reactor or a continuous stirred tank reactor (CSTR). The reactor can be agitated, for example by stirring or by using static mixing.

After the 5-(chloromethyl)furfural is produced, it can be separated from the reaction mixture resulting from step (c) by liquid-liquid extraction. Such liquid-liquid extraction can suitably be carried out in a separate extraction vessel subsequent to the dehydration reactor.

Preferably, however, such liquid-liquid extraction is carried out in-situ. By an in-situ extraction is herein understood that the 5-(chloromethyl)furfural is extracted into an extraction solvent present within the reaction mixture.

Preferably, the reactor in step (c) is therefore further suitable for carrying out a liquid-liquid extraction. For example, step (c) may comprise heating at least part of the, hydrochloric acid-containing, aqueous hydrolysate solution, together with an extraction solvent, in an agitated (for example stirred or mixed) reactor, to a temperature equal to or more than 60° C., more preferably equal to or more than 70° C., to thereby produce 5-(chloromethyl)furfural. Subsequently at least part of such produced 5-(chloromethyl)furfural is extracted, in situ, into the extraction solvent, to thereby produce a 5-(chloromethyl)furfural-containing extraction solvent. Preferably such in-situ extraction is thus carried out continuously and/or simultaneously (i.e. alongside) with the dehydration reaction.

Advantageously step (c) is carried out in a continuously stirred tank reactor (CSTR). Suitably such CSTR may contain both (at least part of) the aqueous hydrolysate solution as well as an extraction solvent. When applied in a continuous or semi-continuous process, such a CSTR may advantageously be combined with a separate continuous liquid-liquid separator, such as for example an in-line liquid-liquid separator using a hydrophobic membrane, a hydrocyclone or a swirl separator.

It can, however, also be advantageous to carry out step (c) in a, preferably biphasic, co-current or counter-current flow reactor, where a flow of at least part of the aqueous hydrolysate solution is contacted, at a temperature of equal to or more than 60° C., more preferably equal to or more than 70° C., respectively co-currently or counter-currently, with a flow of extraction solvent.

Without wishing to be bound by any kind of theory, it is believed that by in-situ, and optionally counter-currently, contacting the aqueous hydrolysate solution with the extraction solvent, the 5-(chloromethyl)furfural can be conveniently extracted into the extraction solvent, immediately after its preparation. That is, when the reaction is proceeding in the presence of the extraction solvent any 5-(chloromethyl)furfural can simultaneously be extracted into the extraction solvent.

Step (c) is advantageously carried out at a relatively high temperature, i.e. at a temperature equal to or more than 60° C., more preferably a temperature equal to or more than 70° C., and even more preferably a temperature equal to or more than 80° C. For practical purposes step (c) can suitably be carried out at a temperature in the range from equal to or more than 60° C., more preferably equal to or more than 70° C., even more preferably equal to or more than 80° C., to equal to or less than 120° C., more preferably equal to or less than 110° C.

Step (c) can be carried out at a wide range of pressures. Preferably, however, step (c) is carried out at a pressure in the range from 0.1 MegaPascal to 10.0 MegaPascal.

Preferably process step (c) is continued for a period ranging from equal to or more than 0.25 hours, more preferably from equal to or more than 0.50 hours, to equal to or less than 10.00 hours, more preferably to equal to or less than 4.00 hours, and still more preferably to equal to or less than 2.00 hours.

The extraction solvent is preferably an organic extraction solvent in which organic extraction solvent, at the temperature and pressure applied during step (c), 5-(chloromethyl) furfural has a higher solvability than in water.

The extraction solvent is preferably an organic extraction solvent:

which organic extraction solvent has a boiling temperature, at the pressure applied during step (c), which is lower than the temperature applied during step (c); and/or which organic extraction solvent, at the temperature applied during step (c), is essentially immiscible with water; and/or which organic extraction solvent, at the temperature and pressure applied during step (c), is essentially not reactive with hydrochloric acid.

By an organic extraction solvent is herein understood an extraction solvent comprising compounds having hydrocarbon bonds. By a hydrocarbon bond is herein understood a covalent bonding between a hydrogen and a carbon atom. By essentially immiscible with water is herein understood an organic extraction solvent having a solubility in water of less than 10 grams per 100 grams of water.

The extraction solvent can for example be a non-polar solvent or an aprotic polar solvent. Preferably the extraction solvent is an organic extraction solvent, more preferably an organic extraction solvent selected from the group consisting of: C6-C10 aromatic hydrocarbons, C1-C10 chlorinated hydrocarbons and C3-C10 ketones and mixtures of two or more thereof. By a Cx compound is herein understood a compound comprising "x" carbon atoms. By a Cx-Cz compound is herein understood a compound comprising in the range from "x" to "z" carbon atoms. Suitably the extraction solvent can be selected from the group consisting of: diethyl ether, diisopropyl ether, ethyl acetate, pentane, hexane, heptane, octane, decane, dodecane, cyclohexane, benzene, toluene, xylene, chloroform, dichloromethane, dichloroethane, carbon tetrachloride, trichloromethane (chloroform), methyl tert-butyl ether, and mixtures of two or more thereof. More preferably an aromatic extraction solvent is used, more preferably selected from the group consisting of benzene, toluene and xylene.

When the heating in step (c) is carried out in the presence of the extraction solvent and when the 5-(chloromethyl) furfural is suitably extracted with such extraction solvent in-situ, an extraction solvent having a boiling point above 70° C. at the applied pressure is preferred.

More preferably the extraction solvent is therefore selected from the group consisting of heptane, octane, decane, dodecane, toluene, xylene, 1,2-dichloroethane, carbon tetrachloride and mixtures of two or more thereof.

Most preferably, the extraction solvent is toluene or 1,2-dichloroethane.

Preferably the volume ratio between the, hydrochloric acid-containing, aqueous hydrolysate solution and the extraction solvent lies in the range from 10:1 to 1:10, more preferably in the range from 5:1 to 1:5.

Preferably the extraction solvent is either more or less dense than water. This allows the extraction solvent to be easily separated from water by simple phase separation. In addition this allows for a suitable operation in a, preferably biphasic, counter-current or co-current biphasic continuous flow reactor.

The yielded 5-(chloromethyl)furfural-containing extraction solvent can subsequently be separated from the aqueous hydrolysate solution and/or the reaction mixture.

Such separation can be achieved in any manner known to be suitable therefore by the person skilled in the art. Such separation may or may not include cooling, phase separation, membrane separation, settling and/or centrifugation.

Any separated 5-(chloromethyl)furfural-containing extraction solvent may optionally be dried to remove any residual water.

To remove any residual 5-(chloromethyl)furfural from the remaining aqueous hydrolysate solution and/or the reaction mixture, the remaining aqueous hydrolysate solution and/or the reaction mixture may optionally be mixed and/or washed with additional extraction solvent to extract such residual 5-(chloromethyl)furfural.

Prefereably step (c) is carried out in a biphasic counter-current flow reactor, where a flow of at least part of the hydrochloric acid-containing, aqueous hydrolysate solution is contacted counter-currently with a flow of extraction solvent. When a biphasic counter-current flow reactor is used, where a flow of at least part of the aqueous hydrolysate solution is contacted counter-currently with a flow of extraction solvent, the 5-(chloromethyl)furfural-containing extraction solvent is already separated within the reactor from the aqueous hydrolysate solution and/or the reaction mixture.

The 5-(chloromethyl)furfural may or may not be isolated from the 5-(chloromethyl)furfural-containing extraction solvent.

Preferably the process further comprises:
(i) isolating or separating the 5-(chloromethyl)furfural from the extraction solvent and converting the isolated or separated 5-(chloromethyl)furfural into 2,5 di-formylfuran, 5-(hydroxymethyl)furfural and/or an 5-(alkoxymethyl)furfural; or
(ii) retrieving the 5-(chloromethyl)furfural-containing extraction solvent, suitably as a whole, and converting the 5-(chloromethyl)furfural, in the presence of the extraction solvent, into 2,5 diformylfuran, 5-(hydroxymethyl)furfural and/or an 5-(alkoxymethyl)furfural.

Preferably the 5-(chloromethyl)furfural is processed further in a non-isolated form, in combination with the extraction solvent. That is, preferably the 5-(chloromethyl)furfural-containing extraction solvent is further processed as a whole.

Alternatively, 5-(chloromethyl)furfural is first isolated from the extraction solvent, before further processing such 5-(chloromethyl)furfural.

The 5-(chloromethyl)furfural can be isolated from the extraction solvent in any manner known by the person skilled in the art, for example by evaporation and/or distillation. After removal of the 5-(chloromethyl)furfural, the extraction solvent may be recycled for re-use. The isolated 5-(chloromethyl)furfural may be converted with conventional techniques as known in the art into for example 2,5 di-formylfuran (DFF), 5-(hydroxymethyl)furfural (HMF) and/or 5-(alkoxymethyl)furfurals, such as 5-(methoxymethyl)furfural (MMF) or 5-(ethoxymethyl)furfural (EMF).

As indicated, advantageously it is not necessary to immediately isolate the 5-(chloromethyl)furfural from the extraction solvent. Any produced 5-(chloromethyl)furfural-containing extraction solvent may suitably be further processed without separating the 5-(chloromethyl)furfural.

For example, the extraction solvent can advantageously be used as a solvent in:
a process wherein the 5-(chloromethyl)furfural is reacted with an alkanol to produce an 5-(alkoxymethyl)furfural ether;
a process wherein the 5-(chloromethyl)furfural is reacted with water to produce 5-(hydroxymethyl)furfural; or
a process wherein the 5-(chloromethyl)furfural is converted into 2,5 di-formylfuran.

When the 5-(chloromethyl)furfural is reacted with an alkanol, such alkanol is preferably selected from the group consisting of methanol, ethanol, propanol, iso-propanol, butanol, iso-butanol and tert-butanol.

The present invention therefore also provides a process for the production of 5-(alkoxymethyl)furfural comprising:

a process for the conversion of a solid lignocellulosic material containing hemicellulose, cellulose and lignin, the process including the following steps:

(a) hydrolyzing at least part of the hemicellulose and at least part of the cellulose of the solid lignocellulosic material at a temperature equal to or less than 30° C. with an aqueous hydrochloric acid solution, containing in the range from equal to or more than 40.0 wt. % to equal to or less than 51.0 wt. % hydrochloric acid, based on the combined weight amount of water and hydrochloric acid in such aqueous hydrochloric acid solution; yielding a hydrochloric acid-containing, aqueous hydrolysate solution;

(b) separating the hydrochloric acid-containing, aqueous hydrolysate solution from the lignin; and (c) heating at least part of the hydrochloric acid-containing, aqueous hydrolysate solution to a temperature equal to or more than 60° C., preferably equal to or more than 70° C., yielding a product solution containing 5-(chloromethyl) furfural, and extracting the 5-(chloromethyl)furfural from such product solution into an extraction solvent; and further comprising:

retrieving the 5-(chloromethyl)furfural-containing extraction solvent; and reacting the 5-(chloromethyl)furfural, in the presence of the extraction solvent, preferably at a temperature in the range from equal to or more than 10° C. to equal to or less than 90° C., more preferably equal to or less than 50° C., with an alkanol, preferably selected from the group consisting of ethanol, propanol, iso-propanol, butanol, iso-butanol and tert-butanol, suitably yielding an 5-(alkoxymethyl) furfural.

The step of retrieving the 5-(chloromethyl)furfural-containing extraction solvent can optionally be combined with step (c), for example when using a biphasic, co-current or counter-current, flow reactor. Further preferences for carrying out the reaction of the 5-(chloromethyl)furfural can be found for example in Estonian patent application EE2013/0003A. Most preferably the alkanol is ethanol, allowing the process to thereby produce 5-(ethoxymethyl)furfural (EMF). Further preferences for steps (a), (b) and (c) are as described herein above.

Further, the present invention also provides a process for the production of 5-(methoxymethyl)furfural comprising:

a process for the conversion of a solid lignocellulosic material containing hemicellulose, cellulose and lignin, the process including the following steps:

(a) hydrolyzing at least part of the hemicellulose and at least part of the cellulose of the solid lignocellulosic material at a temperature equal to or less than 30° C. with an aqueous hydrochloric acid solution, containing in the range from equal to or more than 40.0 wt. % to equal to or less than 51.0 wt. % hydrochloric acid, based on the combined weight amount of water and hydrochloric acid in such aqueous hydrochloric acid solution; yielding a hydrochloric acid-containing, aqueous hydrolysate solution;

(b) separating the hydrochloric acid-containing, aqueous hydrolysate solution from the lignin; and (c) heating at least part of the hydrochloric acid-containing, aqueous hydrolysate solution to a temperature equal to or more than 60° C., preferably equal to or more than 70° C., yielding a product solution containing 5-(chloromethyl) furfural, and extracting the 5-(chloromethyl)furfural from such product solution into an extraction solvent; and further comprising:

retrieving the 5-(chloromethyl)furfural-containing extraction solvent; and reacting the 5-(chloromethyl)furfural, in the presence of the extraction solvent, preferably at a temperature in the range from equal to or more than 10° C. to equal to or less than 90° C., more preferably equal to or less than 50° C., with methanol, suitably yielding a 5-(methoxymethyl)furfural.

The step of retrieving the 5-(chloromethyl)furfural-containing extraction solvent can optionally be combined with step (c), for example when using a biphasic, co-current or counter-current, flow reactor. Further preferences for carrying out the reaction of the 5-(chloromethyl)furfural can be found for example in Estonian patent application EE2013/0003A. Further preferences for steps (a), (b) and (c) are as described herein above.

Still further, the present invention also provides a process for the production of 5-(hydroxymethyl)furfural comprising:

a process for the conversion of a solid lignocellulosic material containing hemicellulose, cellulose and lignin, the process including the following steps:

(a) hydrolyzing at least part of the hemicellulose and at least part of the cellulose of the solid lignocellulosic material at a temperature equal to or less than 30° C. with an aqueous hydrochloric acid solution, containing in the range from equal to or more than 40.0 wt. % to equal to or less than 51.0 wt. % hydrochloric acid, based on the combined weight amount of water and hydrochloric acid in such aqueous hydrochloric acid solution; yielding a hydrochloric acid-containing, aqueous hydrolysate solution;

(b) separating the hydrochloric acid-containing, aqueous hydrolysate solution from the lignin; and (c) heating at least part of the hydrochloric acid-containing, aqueous hydrolysate solution to a temperature equal to or more than 60° C., preferably equal to or more than 70° C., yielding a product solution containing 5-(chloromethyl) furfural, and extracting the 5-(chloromethyl)furfural from such product solution into an extraction solvent; and further comprising:

retrieving the 5-(chloromethyl)furfural-containing extraction solvent; and reacting the 5-(chloromethyl)furfural, in the presence of the extraction solvent, preferably at a temperature in the range from equal to or more than 10° C. to equal to or less than 90° C., more preferably equal to or less than 50° C., with water, suitably yielding a 5-(hydroxymethyl)furfural.

The step of retrieving the 5-(chloromethyl)furfural-containing extraction solvent can optionally be combined with step (c), for example when using a biphasic, co-current or counter-current, flow reactor. Further preferences for steps (a), (b) and (c) are as described herein above.

Even further, the present invention also provides a process for the production of 2,5 di-formylfuran comprising:

a process for the conversion of a solid lignocellulosic material containing hemicellulose, cellulose and lignin, the process including the following steps:

(a) hydrolyzing at least part of the hemicellulose and at least part of the cellulose of the solid lignocellulosic material at a temperature equal to or less than 30° C. with an aqueous hydrochloric acid solution, containing in the range from equal to or more than 40.0 wt. % to equal to or less than 51.0 wt. % hydrochloric acid, based on the combined weight amount of water and hydrochloric acid in such aqueous hydrochloric acid solution; yielding a hydrochloric acid-containing, aqueous hydrolysate solution;

(b) separating the hydrochloric acid-containing, aqueous hydrolysate solution from the lignin; and (c) heating at least part of the hydrochloric acid-containing, aqueous hydrolysate solution to a temperature equal to or more than 60° C., preferably equal to or more than 70° C., yielding a product solution containing 5-(chloromethyl) furfural, and extracting the 5-(chloromethyl)furfural from such product solution into an extraction solvent; and further comprising:

retrieving the 5-(chloromethyl)furfural-containing extraction solvent; and oxydizing the 5-(chloromethyl)furfural, in the presence of the extraction solvent, to 2,5 diformylfuran.

The step of retrieving the 5-(chloromethyl)furfural-containing extraction solvent can optionally be combined with step (c), for example when using a biphasic, co-current or counter-current, flow reactor. Further preferences for steps (a), (b) and (c) are as described herein above.

The above processes advantageously allow one to heat up and convert the saccharides resulting from hemicellulose and/or cellulose into useful products, without wasting energy on heating the lignin. In addition the above processes advantageously allow one to avoid any cumbersome and expensive steps to isolate the 5-(chloromethyl)furfural from the extraction solvent.

When producing a 5-(alkoxymethyl) furfural, a 5-(hydroxymethyl)furfural and/or diformylfurfural from the 5-(chloromethyl)furfural, hydrochloric acid is suitably again produced as a side-product. Such hydrochloric acid may advantageously be used in a direct recycle to step (a). More advantageously, such hydrochloric acid can be added as supplemental hydrochloric acid to a residual, hydrochloric acid-containing, aqueous solution being recycled from step (c) to step (a). Such recycles of hydrochloric acid and residual, hydrochloric acid-containing, aqueous solution reduce the making of chlorine-containing waste and contribute to the economics, efficiency and sustainability of the process of the invention.

Non-limiting FIG. 1 below illustrates an example of the process according to the invention.

Figure 1:
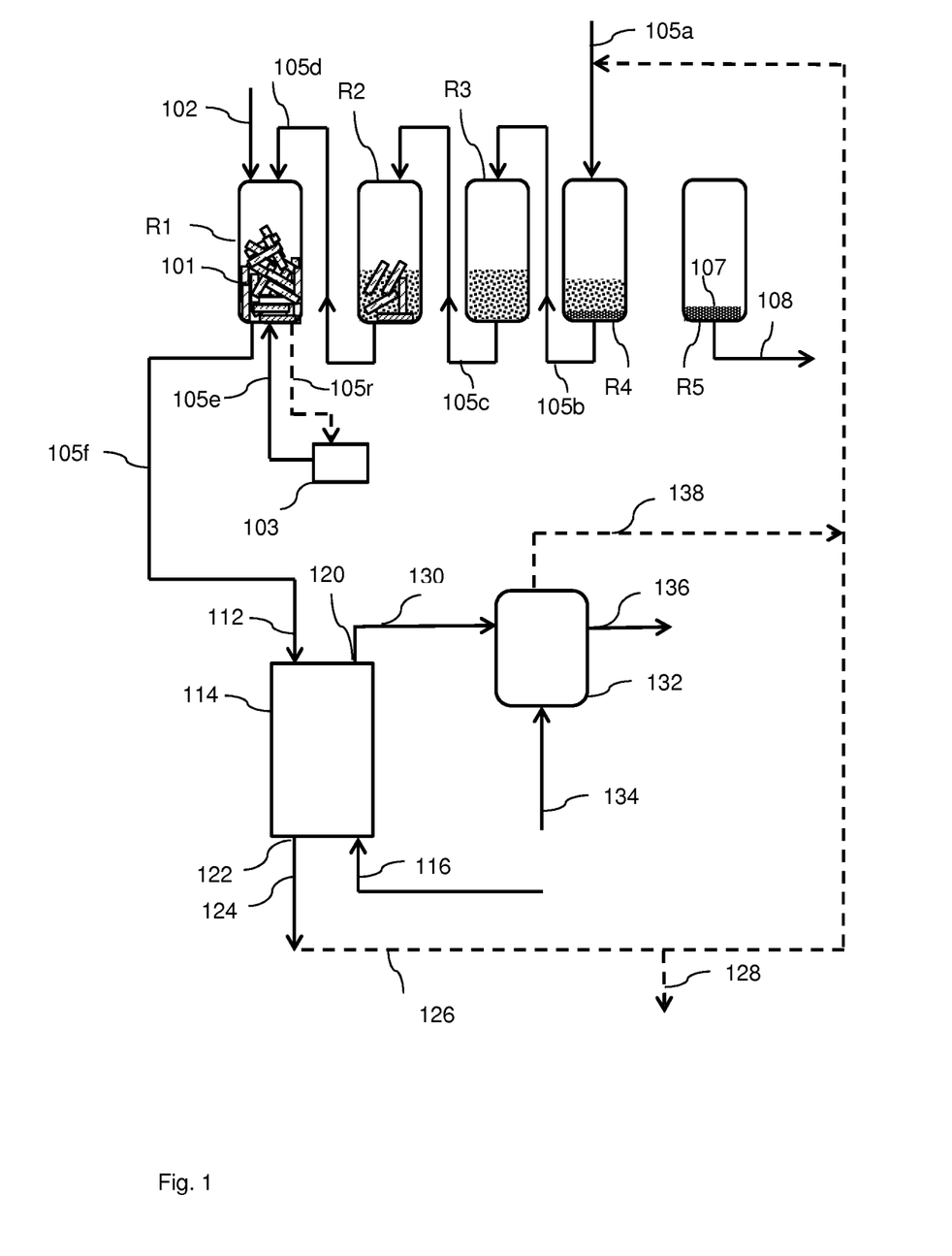
FIG. 1 illustrates a first cycle, starting at a time "t", of a process according to the invention wherein step (a) is carried out semi-continuously in a plurality of reactors and wherein step (c) of the process is carried out continuously in the presence of an extraction solvent in a counter-current biphasic continuous flow reactor.

FIG. 1 shows a process according to the invention wherein step (a) is carried out semi-continuously in a plurality of reactors connected in series (i.e. a reactor sequence) and wherein step (c) of the process is carried out continuously in the presence of an extraction solvent in a counter-current biphasic continuous flow reactor.

In the process as illustrated in FIG. 1, step (a) is carried out in a reactor sequence of 5 hydrolysis reactors (R1 to R5). The hydrolysis reactors are operated at a temperature of 20° C. The process is operated in a sequence of cycles with an 8 hour cycle period.

FIG. 1 illustrates a new cycle, starting at time "t". At the start of a new cycle, dried wood chips (101) have just been loaded into reactor (R1) via solid inlet line (102). Reactor (R1) is subsequently flooded with an aqueous intermediate hydrolysate solution (105e) coming from a storage vessel (103).

Hereafter reactors (R1), (R2), (R3) and (R4) shift into a hydrolysis stage, whilst reactor (R5) shifts into a residue unloading stage.

In a first part of a new cycle, a plug of fresh aqueous hydrochloric acid solution (105a), having a hydrochloric acid concentration of 42.0 wt. % and containing essentially no saccharides yet, is introduced into reactor (R4), thereby pushing forward a plug of aqueous intermediate hydrolysate solution (105b), containing hydrochloric acid, but also containing already some saccharides (i.e. derived from material that was residing in reactor (R4), from reactor (R4) into reactor (R3).

This plug of aqueous intermediate hydrolysate solution (105b) in its turn pushes forward a second plug of aqueous intermediate hydrolysate solution (105c), containing hydrochloric acid, but also containing saccharides (i.e. derived from, optionally partially hydrolyzed, lignocellulosic material that was residing in previous reactors), from reactor (R3) into reactor (R2).

This second plug of aqueous intermediate hydrolysate solution (105c) in its turn pushes forward a third plug of aqueous intermediate hydrolysate solution (105d), containing hydrochloric acid, but also containing saccharides (i.e. derived from, optionally partially hydrolyzed, lignocellulosic material that was residing in previous reactors), from reactor (R2) into reactor (R1).

Whilst being pushed from reactor (R4) into reactor (R3) and further into reactor (R2) and subsequently into reactor (R1), the aqueous intermediate hydrolysate solution absorbs more and more saccharides from the material remaining in such reactors from previous stages. The saccharide concentration of the aqueous intermediate hydrolysate solution advantageously increases, thus allowing a saccharide concentration to be obtained, that is higher than the saccharide concentration that could be obtained in a batch-process.

The plug of aqueous intermediate hydrolysate solution (105d), pushes the final aqueous hydrolysate solution (105f) out from reactor (R1).

The final, hydrochloric acid-containing, aqueous hydrolysate solution (105f) pushed out of reactor (R1) is conveniently forwarded via liquid outlet line (112) to a counter-current biphasic continuous flow reactor (114).

In the part of the cycle wherein a fresh plug of aqueous hydrochloric acid solution is introduced, residue (107), containing mostly lignin, is removed from the last reactor (R5) via solid outlet line (108).

At the end of the cycle aqueous intermediate hydrolysate solution is withdrawn from reactor (R4) and pushed into reactor (R3), separating aqueous intermediate hydrolysate solution from a residue, which residue is left behind in reactor (R4). The plug of withdrawn aqueous intermediate hydrolysate solution withdrawn from reactor (R4) and pushed into reactor (R3) pushes further forward the plugs in the reactors (R3) and (R2). The plug of aqueous intermediate hydrolysate solution residing in reactor (R2) is pushed out of reactor (R2) into reactor (R1). The last plug of aqueous intermediate hydrolysate solution (105r) residing in reactor (R1) is pushed out of reactor (R1) and stored into storage vessel (103) as illustrated by the dashed line. At the same time reactor (R5) can be loaded with a new batch dried wood chips.

The cycle has now been completed and all reactors have shifted position in the reactor sequence. That is, reactor (R5) has shifted into the position of reactor (R1), reactor (R1) has shifted into the position of reactor (R2), reactor (R2) has shifted into the position of reactor (R3), reactor (R3) has shifted into the position of reactor (R4), reactor (R4) has shifted into the position of reactor (R5). As indicated, the above cycle takes about 8 hours. A subsequent cycle can now be started.

Figure 2:
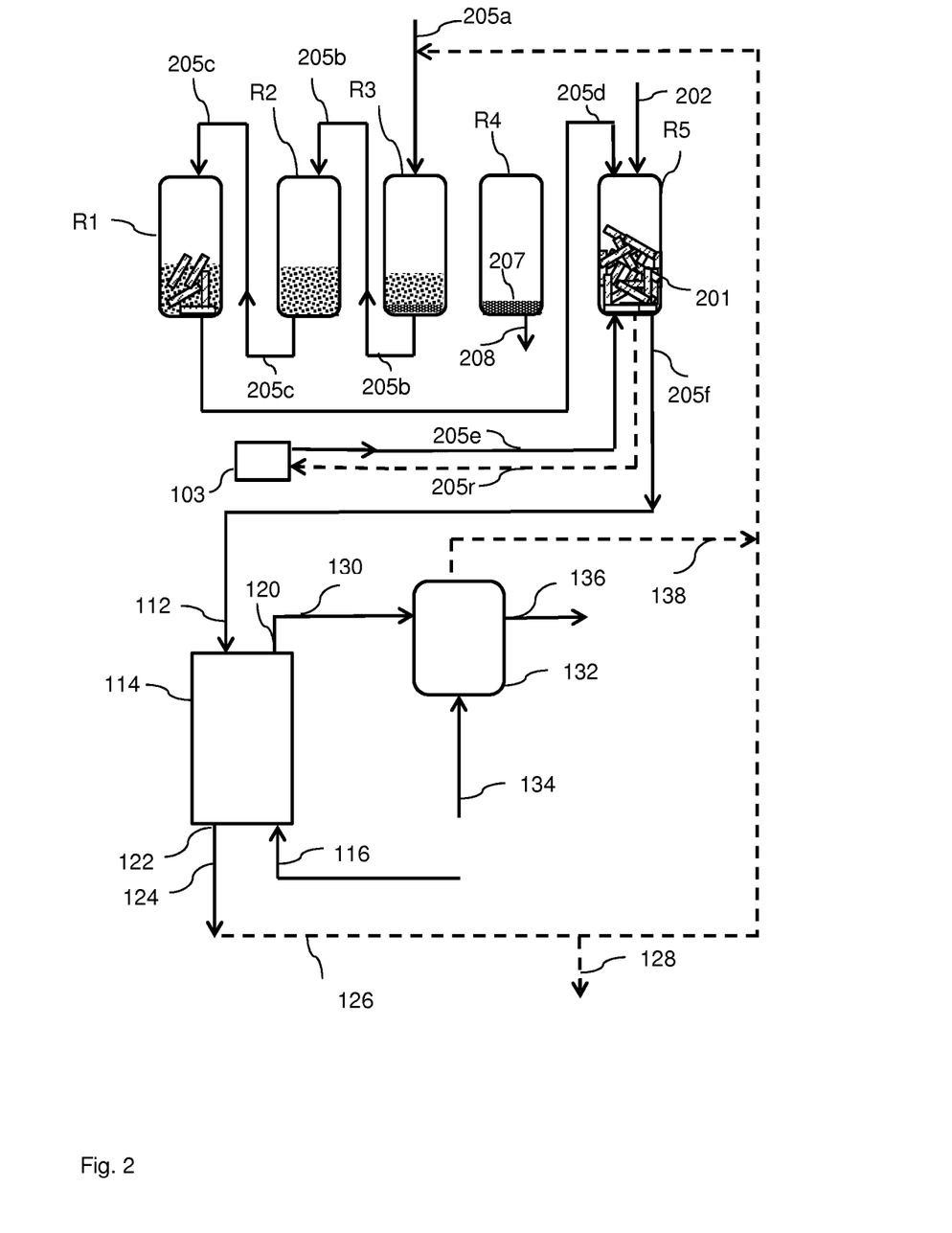
FIG. 2 illustrates a second cycle, starting at a time "t+8 hours" of the same process as FIG. 1.

FIG. 2 illustrates a subsequent cycle, starting at a time "t+8 hours". The dried wood chips in reactor (R5) can be flooded with aqueous intermediate hydrolysate solution (205e) withdrawn from storage vessel (103). This is the same aqueous intermediate hydrolysate solution that was stored in such storage vessel (103) as aqueous intermediate hydrolysate solution (105r) in the previous cycle of FIG. 1. Hereafter the subsequent cycle can be carried out in a similar manner as described above for the preceding cycle. The numerals (201), (202), (205a-f) and (205r), (207) and (208) refer to features similar to the features referred to by numerals (101), (102), (105a-f) and (105r), (107) and (108) in FIG. 1.

After a total of 5 cycles, and a period of 40 hours, the situation is again exactly as in FIG. 1.

In the above, all the hydrochloric acid concentrations are on a weight basis, based on the combined weight amount of water and hydrochloric acid.

As illustrated in both FIG. 1 and FIG. 2, final, hydrochloric acid-containing, aqueous hydrolysate solution (105f), respectively (205f) is pushed out of reactor (R1) and forwarded via liquid outlet line (112) to a counter-current biphasic continuous flow reactor (114). In such counter-current biphasic continuous flow reactor, the hydrochloric acid-containing, aqueous hydrolysate solution is subsequently contacted with an extraction solvent, such as toluene, supplied via liquid inlet line (116). The counter-current biphasic continuous flow reactor (114) is operated at 90° C.

From the top of the counter-current biphasic continuous flow reactor (114) a stream of 5-(chloromethyl)furfural-containing extraction solvent (120) is obtained via liquid outlet line (130) and from the bottom of the counter-current biphasic continuous flow reactor (114) a stream comprising residual, hydrochloric acid-containing, aqueous solution (122) is obtained via liquid outlet line (124).

The bottom stream (122) comprising residual, hydrochloric acid-containing aqueous solution is optionally recycled via recycle line (126) (illustrated as a dashed line) to be reused as at least part of aqueous hydrochloric acid solution described above. If so desired, minor impurities can be removed and optionally a bleed stream (128) can be present (both illustrated as a dashed line).

The top stream of reactor (114) containing 5-(chloromethyl)furfural-containing extraction solvent (120) is forwarded via liquid outlet line (130) to a further reactor (132). In the further reactor (132) the 5-(chloromethyl)furfural, in the presence of the extraction solvent, is reacted with ethanol provided via liquid inlet line (134) at a temperature of 50° C. to thereby produce 5-(ethoxymethyl)furfural and a hydrochloric acid side-product. The 5-(ethoxymethyl)furfural can be withdrawn from reactor (132) via liquid outlet line (136) and processed further. The hydrogen chloride containing side-product can conveniently be recycled via recycle line (138) to be reused as supplemental hydrochloric acid to produce at least part of the aqueous hydrochloric acid solution described above.

The invention is further illustrated by the following non-limiting examples.

EXAMPLE 1

Hydrolysis of Pine Wood

An amount of pine wood was hydrolyzed by treatment with an aqueous solution containing about 42 wt % hydrochloric acid (HCl) at room temperature (about 20° C.). After treatment the liquid was separated from the remaining residue, resulting in an hydrochloric acid-containing, aqueous hydrolysate solution, hereafter called hydrolysate product.

The hydrolysate product contained components as illustrated in Table 1.

TABLE 1

Composition of the hydrolysate product.

| Component | Content (wt %) |
|---|---|
| Cellobiose | 0.098 |
| Galacturonic acid | 0.038 |
| Glucose | 5.76 |
| Mannose | 0.50 |
| Arabinose | 0.019 |
| Glucuronic acid | 0.10 |

EXAMPLE 2

Conversion of the Hydrolysate Product

The hydrolysate product obtained in example 1 was used as the substrate, without purification, for the conversion to 5-chloromethyl furfural (CMF). Both glucose and mannose were considered to be substrates for 5-chloromethyl formation. Experiments were run in blocks of 12 parallel 7.7 mL stainless steel batch reactors with Teflon liners using magnetic stirring at 1200 rpm. An amount of the hydrolysate substrate as listed in Table 2 was weighed in the reactor after which extraction solvent was added. The extraction solvent was toluene for all experiments. This was followed by immediate insertion into the heating block, where the reactor contents were heated to a temperature (T) as listed in Table 2. After the reaction time (t) as indicated in Table 2, the blocks were removed and cooled in an ice bath. Subsequently the reactor blocks were opened and the contents transferred to 8 mL glass vials. The phases were separated with the aqueous layer being washed twice with 0.5 mL toluene. Both phases were worked up for analysis. The organic layer containing 5-chloromethylfurfural (CMF) and furfural was analyzed using gas chromatography. The aqueous layer containing hydroxymethylfurfural (HMF) was analyzed using ultra performance liquid chromatography. Table 2 shows the results obtained with the hydrolysate substrate as feed.

Table 3 shows comparative experiments, carried out in a same way as above, with cellulose dissolved in aqueous solution containing about 37 wt % hydrochloric acid (HCl) as substrate. The results using the hydrolysate substrate provide yields as high as 43.5% in CMF. The difference with cellulose as the substrate is substantial, with the highest yield under comparable conditions for cellulose being about 24.3% CMF yield. This clearly shows that the two-step conversion from cellulosic feed according to the process of the invention is significantly better.

TABLE 2

Conversion of hydrolysate substrate

| Hydrolysate substrate (mg) | mannose and glucose present (mg) | volume extraction solvent (μl) | T (° C.) | t (h) | Yield HMF (mol %) | Yield furfural (mol %) | Yield CMF (mol %) | Conversion (%) |
|---|---|---|---|---|---|---|---|---|
| 653.2 | 40.9 | 1000 | 80 | 2 | 3.2 | 0.23 | 40.9 | 95.2 |
| 630.7 | 39.5 | 1000 | 80 | 2 | 3.1 | 0.22 | 39.6 | 96.1 |
| 584.5 | 36.6 | 1000 | 80 | 2 | 2.8 | 0.20 | 43.5 | 95.9 |
| 626.4 | 39.2 | 1000 | 80 | 2 | 3.1 | 0.21 | 42.5 | 96.2 |
| 584.0 | 36.5 | 1000 | 100 | 1 | 2.2 | 0.21 | 36.3 | 99.4 |
| 563.1 | 35.2 | 1000 | 100 | 1 | 2.8 | 0.22 | 35.0 | 99.4 |
| 606.0 | 37.9 | 1000 | 100 | 1 | 3.3 | 0.24 | 29.2 | 98.4 |
| 574.0 | 35.9 | 1000 | 100 | 1 | 2.5 | 0.22 | 34.1 | 99.6 |

TABLE 3

Conversion of cellulose substrate

| Cellulose mass (mg) | HCL (37 wt %) Solvent volume (μl) | Toluene Extraction solvent volume (μl) | T (° C.) | t (h) | Yield HMF (%) | Yield Furfural (%) | Yield CMF (%) |
|---|---|---|---|---|---|---|---|
| 5.6 | 500 | 1000 | 100 | 1 | 3.3 | 0.15 | 24.3 |
| 5.7 | 500 | 1000 | 100 | 1 | 2.2 | 0.12 | 23.2 |
| 50.2 | 500 | 1000 | 100 | 1 | 3.2 | 0.11 | 22.4 |
| 50.4 | 500 | 1000 | 100 | 3 | 1.2 | 0.02 | 11.8 |
| 24.7 | 500 | 1000 | 80 | 2 | 1.4 | 0.06 | 15.1 |
| 50.4 | 500 | 1000 | 80 | 2 | 2.2 | 0.06 | 13.1 |

EXAMPLE 4

Conversion of 5-Chloromethylfurfural

An amount of 5-Chloromethylfurfural (CMF) as listed in Table 3 was weighed in 1.8 mL HPLC vials and dissolved in an amount of dichloromethane (DCM) solvent as listed in Table 3. To such solution of CMF in dichloromethane solvent, methanol (MeOH) was added in an amount as listed in Table 3. Directly after addition of the methanol to the reaction mixture, the vials were heated to a temperature (T) as listed in Table 3 to start the reaction. After a reaction time (t) as listed in Table 3, the vials were directly cooled in an ice bath, followed by work-up for analysis (gas chromatography and ultra performance liquid chromatography). Table 4 provides an overview of the conversion of 5-Chloromethylfurfural (CMF) and the yields and selectivity towards 5-(methoxymethyl)furfural (MMF).

TABLE 4

| Amount CMF (mg) | T (° C.) | t (h) | DCM (μL) | MeOH (μL) | Yield MMF (mol %) | Conversion CMF (mol %) | Selectivity MMF (mol %) |
|---|---|---|---|---|---|---|---|
| 10.1 | 50 | 4 | 350 | 150 | 84.6 | 97.5 | 86.8 |
| 10.9 | 50 | 4 | 250 | 250 | 79.7 | 98.6 | 80.8 |
| 11.5 | 50 | 2 | 250 | 250 | 78.5 | 98.2 | 79.9 |
| 10.3 | 30 | 4 | 250 | 250 | 73.3 | 98.5 | 74.4 |
| 11.7 | 50 | 2 | 350 | 150 | 64.7 | 91.9 | 70.3 |
| 11.9 | 30 | 3 | 250 | 250 | 57.4 | 60.6 | 94.7 |

The invention claimed is:

1. A process for the conversion of a solid lignocellulosic material containing hemicellulose, cellulose and lignin, the process including the following steps:

(a) hydrolyzing, at a temperature equal to or less than 40° C., at least part of the hemicellulose and at least part of the cellulose of the solid lignocellulosic material with an aqueous hydrochloric acid solution, containing in the range from equal to or more than 40.0 wt. % to equal to or less than 51.0 wt. % hydrochloric acid, based on the combined weight amount of water and hydrochloric acid in such aqueous hydrochloric acid solution; yielding a hydrochloric acid-containing, aqueous hydrolysate solution;

(b) separating the hydrochloric acid-containing, aqueous hydrolysate solution from the lignin; and (c) heating at least part of the hydrochloric acid-containing, aqueous hydrolysate solution to a temperature equal to or more than 60° C., yielding a product solution containing 5-(chloromethyl)furfural, and extracting the 5-(chloromethyl)furfural from such product solution into an extraction solvent.

2. The process according to claim 1, wherein step (a) is carried out in a plurality of reactors:
wherein one or more portions of aqueous hydrochloric acid solution are moving from one reactor to another and are contacted with, optionally partially hydrolyzed, stationary lignocellulosic material in the reactors.

3. The process according to claim 1,
wherein the aqueous hydrochloric acid solution is contacted counter-currently with the, optionally partially hydrolyzed, solid lignocellulosic material.

4. The process according to claim 1, wherein in step (a) one or more portions of aqueous hydrochloric acid solution form a plug or liquid column, optionally in combination with other fluids, which plug or liquid column is moving continuously or semi-continuously through a plurality of stationary reactors connected in series, each reactor containing an amount of, optionally already partially hydrolyzed, lignocellulosic material.

5. The process according to claim 1, wherein step (a) is carried out in a continuous or semi-continuous manner.

6. The process according to claim 1, wherein step (c) comprises heating at least part of the hydrochloric acid-containing, aqueous hydrolysate solution to a temperature equal to or more than 70° C., to thereby produce 5-(chloromethyl)furfural, and, in-situ, extracting at least part of the produced 5-(chloromethyl)furfural into an extraction solvent, to thereby produce a 5-(chloromethyl)furfural-containing extraction solvent.

7. The process according to claim 6, wherein step (c) is carried out in a biphasic counter-current flow reactor, where a flow of at least part of the hydrochloric acid-containing, aqueous hydrolysate solution is contacted counter-currently with a flow of extraction solvent.

8. The process according to claim 6, wherein the extraction solvent comprises toluene and/or 1,2-dichloroethane.

9. The process according to claim 3, wherein a, hydrochloric acid-containing, residual aqueous solution is obtained, and wherein such, hydrochloric acid-containing, residual aqueous solution is recycled to step (a), optionally after adjusting the hydrochloric acid concentration.

10. The process according to claim 1, wherein the process further comprises:
   (i) isolating the 5-(chloromethyl)furfural from the extraction solvent and converting the isolated 5-(chloromethyl)furfural into 2,5 di-formylfuran, 5-(hydroxymethyl)furfural and/or 5-(alkoxymethyl)furfural; or
   (ii) retrieving the 5-(chloromethyl)furfural-containing extraction solvent and converting the 5-(chloromethyl)furfural, in the presence of the extraction solvent, into 2,5 di-formylfuran, 5-(hydroxymethyl)furfural and/or an 5-(alkoxymethyl)furfural.

11. The process according to claim 1, comprising:
   retrieving the 5-(chloromethyl)furfural-containing extraction solvent; and
   reacting the 5-(chloromethyl)furfural, in the presence of the extraction solvent, with an alkanol selected from the group consisting of ethanol, propanol, iso-propanol, butanol, iso-butanol and tert-butanol, yielding an 5-(alkoxymethyl)furfural.

12. The process according to claim 1, further comprising:
   retrieving the 5-(chloromethyl)furfural-containing extraction solvent; and
   reacting the 5-(chloromethyl)furfural, in the presence of the extraction solvent, with methanol, yielding a 5-(methoxymethyl)furfural.

13. The process according to claim 1, further comprising:
   retrieving the 5-(chloromethyl)furfural-containing extraction solvent; and
   reacting the 5-(chloromethyl)furfural, in the presence of the extraction solvent with water, yielding a 5-(hydroxymethyl)furfural.

14. The process according to claim 1, further comprising:
   retrieving the 5-(chloromethyl)furfural-containing extraction solvent; and
   oxidizing the 5-(chloromethyl)furfural, in the presence of the extraction solvent, to 2,5 di-formylfuran.

15. The process according to claim 1, wherein in step (a) hydrolyzing is at a temperature equal to or less than 30° C.

16. The process according to claim 2, wherein in step (a) the plurality of reactors are connected in series.

17. The process according to 11, wherein the 5-(chloromethyl)furfural is reacted at a temperature in the range from equal to or more than 10° C. to equal to or less than 90° C.

18. The process according to claim 17, wherein the 5-(chloromethyl)furfural is reacted at a temperature equal to or less than 50° C.

19. The process according claim 12, wherein the 5-(chloromethyl)furfural is reacted at a temperature in the range from equal to or more than 10° C. to equal to or less than 90° C.

20. The process according to claim 19, wherein the 5-(chloromethyl)furfural is reacted at a temperature equal to or less than 50° C.

21. The process according to claim 13, wherein the 5-(chloromethyl)furfural is reacted at a temperature in the range from equal to or more than 10° C. to equal to or less than 90° C.

22. The process according to claim 21, wherein the 5-(chloromethyl)furfural is reacted at a temperature equal to or less than 50° C.

* * * * *